United States Patent [19]

O'Lenick, Jr.

[11] Patent Number: 5,932,754
[45] Date of Patent: Aug. 3, 1999

[54] MEADOWFOAM QUATERNARY COMPOUNDS

[75] Inventor: Anthony J. O'Lenick, Jr., Lilburn, Ga.

[73] Assignee: Fan Tech Ltd, Chicago, Ill.

[21] Appl. No.: 09/100,692

[22] Filed: Jun. 19, 1998

Related U.S. Application Data

[63] Continuation-in-part of application No. 09/071,226, May 1, 1998.

[51] Int. Cl.$^6$ ..................................................... C07C 233/00
[52] U.S. Cl. ............................................. 554/52; 554/51
[58] Field of Search ......................................... 584/51, 52

*Primary Examiner*—Deborah D. Carr

[57] ABSTRACT

The present invention deals with the composition of matter and the utilization of certain novel meadowfoam based quaternary compounds. These materials are useful in personal care applications as hair conditioners.

3 Claims, No Drawings

MEADOWFOAM QUATERNARY COMPOUNDS

RELATED APPLICATIONS

This application is a continuation in part of co-pending application Ser. No. 071,226 filed May 1, 1998.

BACKGROUND OF THE INVENTION

1. Field of the Invention

The present invention deals with novel cationic surfactants based upon meadowfoam. The term meadowfoam as used here refers to compounds derived from meadowfoam oil, meadowfoam acid or meadowfoam methyl ester. The introduction of the meadowfoam portion of the molecule into the Quats of the present invention results in improved viscosity building in personal care formulations as well as improved odor stability in the formulation and improved liquidity of the aqueous quaternary compound per se. The term quaternary compound is shortened to "quat" in commonly used surfactant language. We have adopted the use of that shortened form.

2. Description of the Art Practices

Quats are known in the art. Variation of carbon chain lengths in amido quats has direct effect upon the surfactant properties of the quat. While quats based upon short chain fatty acids can be made, they are generally germicidal and irritating to the eyes and skin. They do not provide conditioning effects on hair. The use of fatty acids having more that 12 carbon atoms to make quats result in quats that have little or no conditioning. The selection of a oleyl based quat gives some improved conditioning, but the compound undergoes a process of oxidative instability referred to as rancidity, producing low molecular weight aldehydes with mal odor. The availability of a liquid, oxidatively stable quat that can be used in personal care systems has been elusive prior to the compounds of the present invention.

The recent availability of meadowfoam oil, with it's 20 to 22 carbon atoms and the specific location of it's double bonds, and it's reaction to make quats results in the preparation liquid stable quats, having outstanding emulsifying properties and are very acceptable for use in personal care applications.

None of the prior quats possess the critical meadowfoam carboxy moiety. Molecules of the current invention have the meadowfoam alkyl group in the quat.

THE INVENTION

This invention relates to the use of meadowfoam, weather as the triglyceride, acid or methyl ester to make an meadowfoam amidopropyl dialkyl quat, which has unique, unexpected properties in personal care applications. Specifically, the Quats of the present invention provide a smooth feel on the skin, outstanding viscosity in anionic systems, and are surprisingly oxidatively stable in aqueous personal care formulations.

The unique structure of the meadowfoam results in Quats with oxidative stability heretofore unattainable. The fatty distribution of the oil ranges from 20 to 22 carbons and has unsaturation in specific locations. The oil contains 97% by weight higher unsaturated alkyl groups. Typically, meadowfoam oil contains 60–65% of a twenty carbon mono-carboxy acid having one unsaturation between carbon 5 and 6. Additionally, it contains 12–20% of a twenty two carbon mono-carboxy acid having one unsaturation between either carbon 5 and 6, or carbon 13 and 14 and 15–28% of a twenty two carbon mono-carboxy acid having one unsaturation between both carbon 5 and 6, or carbon 13 and 14. The combination of the fact that there are 20 to 22 carbon atoms in the group leads to lack of volatility, the presence of unsaturation leads to liquidity and the fact that the di-unsaturated moieties are not conjugated leads to outstanding oxidative stability.

Additional aspects of the invention is the application of these materials as personal care applications were the specific properties of the quat having the unique distribution of the meadowfoam on the other result in superior liquidity, lubricity, and outstanding oxidative stability. The products which result from the oxidative breakdown of unstable products are generally aldehydes. These materials have a mal odor and in addition react with fragrances and preservatives causing formulation problems. This fact makes the products of the present invention all the more important to the formulator of personal care products.

Another aspect of the present invention is the meadowfoam amidopropyl dialkyl amine intermediate useful as an intermediate in the preparation of the quats of the present invention and other surfactant derivatives.

The compounds of the current invention are quats derived from meadowfoam conforming to the following structure;

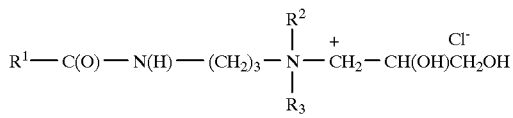

wherein:

$R^1$ is derived from meadowfoam and is;

60–65 % by weight

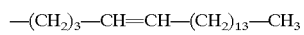

12–20 % by weight a mixture of

and

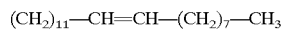

and

15–28 % by weight

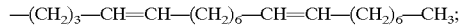

$R^2$ and $R^3$ are methyl or ethyl.

The quat is prepared in a two step reaction. The first step is the preparation of a meadowfoam amidoamine conforming to the following structure:

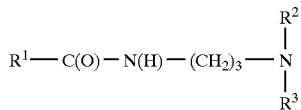

wherein:

$R^1$ is derived from meadowfoam and is;

60–65 % by weight

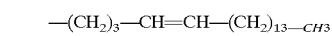

12–20 % by weight a mixture of

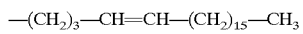

and

and

15–28% by weight

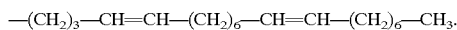

The reaction is as follows:

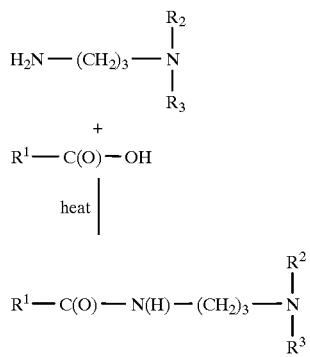

As previously stated another novel aspect of the present invention is the amidoamine intermediate conforming to the following structure:

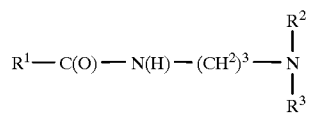

wherein:

$R^1$ is derived from meadowfoam and is;

60–65% by weight —$(CH_2)_3$—CH=CH—$(CH_2)_{13}$—$CH_3$

12–20% by weight a mixture of

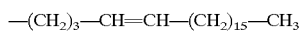

and

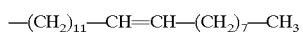

and

15–28% by weight

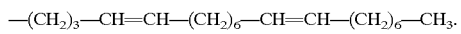

In the second reaction the amidoamine, prepared in the first reaction, is reacted in aqueous solution with of monochlorohydrin as follows:

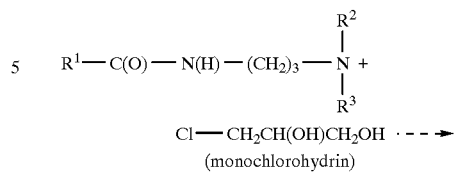

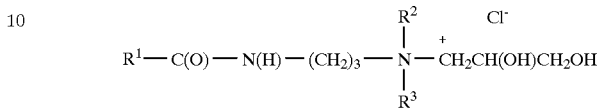

The concentration of the quat in water is generally between 20 and 50% with 35% being preferred. Glycols, lower alcohols and other polar solvents may also be added, if desired.

EXAMPLES

RAW MATERIALS

Meadowfoam Oil

Meadowfoam Oil can be used as a triglyceride, which is the oil as provided, reacted with methanol in processes known to those skilled in the art to make methyl ester, or reacted using technology known in the art to make carboxylic acids. The CAS number of meadowfoam oil is 153065-40-8.

The choice of triglyceride, acid or methyl ester does not change the structure of the resultant ester. It does however change the by-product produced. In the case of the triglyceride, glycerine is produced, in the case of the acid water is produced and in the case of the methyl ester methanol is produced.

Aminopropyl Amine

The compounds conform to the following structure:

EXAMPLE 1

Dimethyl aminopropyl amine

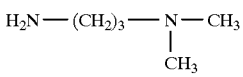

EXAMPLE 2

Diethyl aminopropyl amine

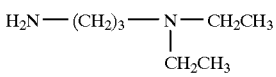

Amidoamine General Procedure—Meadowfoam Oil

To the specified number of grams the specified aminopropyl amine (Examples 1 or 2) is added 354.0 grams of meadowfoam oil. After all ingredients have been charged, under agitation, the temperature of the mass is raised to 180–200 C. This temperature is held for between 1 and 12 hours. The primary amine value decreases to vanishingly low concentrations, and the tertiary amine level becomes theoretical.

The intermediates are clear liquids and are liquid to extraordinary temperatures.

EXAMPLE 3

To 122.0 grams of the specified dialkyl aminopropyl amine (Example 1) is added 354.0 grams of meadowfoam oil. After the two ingredients have been charged, under agitation, the temperature of the mass is raised to 180–200 C. and water is stripped off as formed. The primary amine value decreases to vanishingly low concentrations, and the tertiary amine level becomes theoretical.

EXAMPLE 4

Example 4 is repeated, only this time 150.0 grams of the aminopropyl amine (example 2) is substituted for the aminopropyl amine of example 1.

General Procedure—Meadowfoam Fatty Acid

To the specified number of grams the specified dialkyl aminopropyl amine (Examples 1 and 2) is added 354.0 grams of meadowfoam fatty acid under agitation. The temperature of the mass is raised to 180–200 C. and water is stripped off as formed. This temperature is held for between 1 and 12 hours. The acid value and the primary amine value drops to vanishingly small levels and the tertiary amine level approaches theoretical.

The products are clear liquids and are liquid to extraordinary temperatures.

Amidoamine General Procedure—Meadowfoam Oil

To the specified number of grams the specified aminopropyl amine (Examples 1 or 2) is added 354.0 grams of meadowfoam oil. After all ingredients have been charged, under agitation, the temperature of the mass is raised to 180–200 C. and water is stripped off as formed. The primary amine value decreases to vanishingly low concentrations, and the tertiary amine level becomes theoretical.

The intermediates are clear liquids and are liquid to extraordinary temperatures.

EXAMPLE 5

To 102.0 grams of the specified dialkyl aminopropyl amine (Example 1) is added 354.0 grams of meadowfoam oil. After the two ingredients have been charged, under agitation, the temperature of the mass is raised to 180–200 C. and water is stripped off as formed. The primary amine value decreases to vanishingly low concentrations, and the tertiary amine level becomes theoretical.

EXAMPLE 6

Example 5 is repeated, only this time 150.0 grams of the specified aminopropyl amine (example 2) is substituted for the aminopropyl amine of example 1.

The compounds are the intermediate conforming to the following structure:

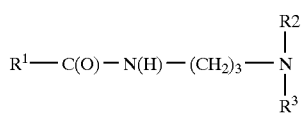

Quat Synthesis

To the specified number of grams of monochlorohydrin is added to the specified amount of water. The solution is heated to 80 C. and the amidoamine (examples 3–6) is added under agitation. The pH is kept between 8–9 by adding NaOH as required. The reaction progress is monitored by the inorganic chloride level, which within 3–4 hours reaches theoretical.

EXAMPLE 7

To the 120.0 grams of monochlorohydrin is added 1,000 grams of water. The solution is heated to 80 C. and 438.0 grams of amidoamine (example 3) is added under agitation. The pH is kept between 8–9 by adding NaOH as required. The reaction progress is monitored by the inorganic chloride level, which within 3–4 hours reaches theoretical.

EXAMPLE 8–15

Example 7 is repeated, only this time the specified amount of the specified amidoamine is added, replacing the amount used in example 7.

|         | Amidoamine |       |
| ------- | ---------- | ----- |
| Example | Example    | Grams |
| 8       | 3          | 438.0 |
| 9       | 4          | 466.0 |
| 10      | 5          | 445.0 |
| 11      | 6          | 475.0 |
| 12      | 3          | 438.0 |
| 13      | 4          | 466.0 |
| 14      | 5          | 445.0 |
| 15      | 6          | 475.0 |

The products produced using the examples 7–15 are clear yellow viscous liquids. The products have outstanding oxidative stability and provide outstanding conditioning to the hair.

I claim:

1. A meadowfoam quat which conforms to the following structure:

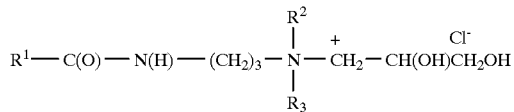

wherein:

$R^1$ is derived from meadowfoam and is

60–65% by weight

12–20% by weight a mixture of

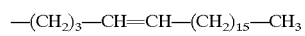

and

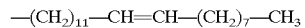

and

15–28 by weight

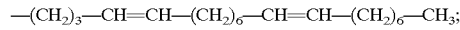

$R^2$ and $R^3$ are methyl or ethyl.

2. A meadowfoam quat of claim 1 wherein $R^2$ is methyl.
3. A meadowfoam quat of claim 1 wherein $R^2$ is ethyl.

* * * * *